United States Patent
Xu

(10) Patent No.: US 10,307,067 B1
(45) Date of Patent: Jun. 4, 2019

(54) WIRELESS LC SENSOR READER

(71) Applicant: W. L. Gore & Associates, Inc., Newark, DE (US)

(72) Inventor: Minghua Xu, Hockessin, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/688,293

(22) Filed: Aug. 28, 2017

Related U.S. Application Data

(60) Provisional application No. 62/380,207, filed on Aug. 26, 2016.

(51) Int. Cl.
*A61B 5/0215* (2006.01)

(52) U.S. Cl.
CPC .................. *A61B 5/0215* (2013.01)

(58) Field of Classification Search
CPC ................................................ A61B 5/0215
See application file for complete search history.

(56) References Cited

U.S. PATENT DOCUMENTS

| | | | |
|---|---|---|---|
| 3,228,030 A | 1/1966 | Moore | |
| 4,206,762 A | 6/1980 | Cosman | |
| 5,480,415 A | 1/1996 | Cox et al. | |
| 6,015,386 A | 1/2000 | Kensey | |
| 6,102,862 A * | 8/2000 | Grunwald | A61B 8/00 600/447 |
| 6,200,268 B1 * | 3/2001 | Vince | A61B 5/02007 600/443 |
| 6,206,835 B1 | 3/2001 | Spillman et al. | |
| 6,254,543 B1 * | 7/2001 | Grunwald | A61B 8/00 600/447 |
| 6,855,115 B2 | 2/2005 | Cardiomems | |
| 7,146,861 B1 | 12/2006 | Cook et al. | |
| 7,181,975 B1 | 2/2007 | Bradley | |
| 7,191,013 B1 | 3/2007 | Miranda et al. | |
| 7,245,117 B1 | 7/2007 | Joy | |
| 7,399,313 B2 | 7/2008 | Brown et al. | |
| 7,452,334 B2 | 11/2008 | Gianchandani et al. | |
| 7,568,394 B1 | 8/2009 | Keilman et al. | |
| 7,647,831 B2 | 1/2010 | Cardiomems | |
| 7,677,107 B2 | 3/2010 | Nunez et al. | |
| 7,955,268 B2 | 6/2011 | Huelskamp | |
| 8,072,310 B1 | 12/2011 | Everhart | |
| 8,187,317 B2 | 5/2012 | Leprince et al. | |
| 8,372,139 B2 | 2/2013 | Bailey et al. | |
| 8,432,265 B2 | 4/2013 | Rowland | |
| 8,493,187 B2 | 7/2013 | Rowland et al. | |

(Continued)

*Primary Examiner* — Lewis G West

(57) ABSTRACT

An energy-efficient, wide-band, and compact wireless sensor reader remotely interrogates an implanted wireless inductive-capacitive (LC) sensor in order to measure a physiologic parameter of interest within a human body. The wireless sensor reader generates an instantaneous, spike-shaped, high-amplitude, low-energy pulse to excite the wireless LC sensor, causing it to emit a ring-down signal. The wireless sensor reader subsequently receives, amplifies, and filters the ring-down signal. Next, the wireless sensor reader digitizes the ring-down signal and transfers the digitized ring-down signal to a processing unit. The processing unit computes a Fast Fourier Transform (FFT) of the digitized ring-down signal and then locates the resonant frequency of the LC sensor using a threshold peak detection technique.

19 Claims, 10 Drawing Sheets

(56) References Cited

U.S. PATENT DOCUMENTS

| | | | |
|---|---|---|---|
| 9,333,365 B2 * | 5/2016 | Zhao | A61B 5/0031 |
| 2004/0082867 A1 | 4/2004 | Esch | |
| 2007/0100215 A1 * | 5/2007 | Powers | A61B 5/0031 600/300 |
| 2008/0033527 A1 | 2/2008 | Nunez et al. | |
| 2008/0177131 A1 * | 7/2008 | Dancu | G09B 23/28 600/36 |
| 2009/0030291 A1 | 1/2009 | O'Brien | |
| 2010/0058583 A1 | 3/2010 | Cros et al. | |
| 2012/0029323 A1 * | 2/2012 | Zhao | A61B 5/0031 600/302 |
| 2013/0165801 A1 | 6/2013 | Min | |
| 2013/0197336 A1 | 8/2013 | Flo et al. | |
| 2014/0080409 A1 * | 3/2014 | Frankland | H02J 5/005 455/41.1 |
| 2014/0128687 A1 | 5/2014 | White et al. | |
| 2014/0273824 A1 | 9/2014 | Fenner et al. | |
| 2014/0296687 A1 | 10/2014 | Irazoqui et al. | |
| 2014/0306807 A1 * | 10/2014 | Rowland | H04Q 9/00 340/10.3 |
| 2014/0350348 A1 | 11/2014 | Tee | |
| 2015/0196225 A1 | 7/2015 | Rusu | |
| 2016/0029956 A1 | 2/2016 | Rowland | |
| 2017/0364905 A1 * | 12/2017 | Hart | G06Q 20/3278 |

\* cited by examiner

WIRELESS LC SENSOR READER

RELATED APPLICATIONS

This application claims priority to U.S. Provisional Application No. 62/380,207, titled WIRELESS LC SENSOR READER and filed on Aug. 26, 2016. The contents of that application (including the Appendix) are incorporated herein by reference for all purposes.

FIELD

Embodiments of the present disclosure generally relate to improved passive LC sensors for medical devices. More specifically, embodiments of the present disclosure relate to sensors and sensor readers for more precisely measuring and monitoring pressure within a blood vessel.

BACKGROUND

Measuring blood pressure is an important diagnostic tool in many medical treatments, especially when treating vascular maladies. For example, aneurysms are often treated by implanting a stent-graft within the aneurysm pocket. Monitoring blood pressure at the stent-graft can be important in tracking patient health and treatment effectiveness. Various pressure sensors have been used for monitoring blood pressure within a vessel, including capacitive pressure sensors. These capacitive pressure sensors are interrogated remotely to extract characteristics that can be used to determine blood pressure.

For example, the resonant frequency of an LC circuit of the sensor may be configured to vary as the pressure varies. By detecting changes in the resonant frequency, changes to blood pressure may be determined. As a result, a sensor reader should have a frequency band wide enough to detect frequencies within a range of interest. To detect changes in the resonant frequency, an external energy field is applied to excite the LC circuit of the sensor. When excited, the LC sensor emits a response signal, which is detected by the sensor reader. The sensor reader uses the response signal to determine the resonant frequency of the LC circuit. However, the intensity of the response signal received by the reader is relatively low, particularly when the sensor is placed deep inside the human body.

Several systems and methods for determining the resonant frequency of an implanted passive LC sensor have been discussed, including the following: U.S. Pat. No. 6,015,386, which excites the LC circuit by a frequency sweep of radio-frequency (RF) energy and then uses a phase detector to locate the resonant frequency; U.S. Pat. No. 7,245,117, which excites the LC circuit by a burst of RF energy at a predetermined frequency or set of frequencies and uses a phased-locked-loop (PLL) circuit to lock onto the sensor's resonant frequency; and U.S. Pat. No. 8,432,265, which discusses an improved reader system using a PLL circuit.

In general, to determine a resonant frequency with the frequency-sweep or phase-lock-loop techniques discussed in these references, the reader may have to fire radio-frequency (RF) excitation pulses many times at a set of predefined frequencies that includes the resonant frequency of the targeted LC circuit; therefore, a wide-band RF signal generator is needed to generate the frequency range of interest. Each excitation pulse may be a sinusoidal burst at a fixed frequency. At the same time, a wide-band RF power amplifier is needed to amplify each fired pulse at each predefined frequency in order to achieve a good signal-to-noise ratio (SNR) in the measurement. However, energy fired at frequencies away from the targeted resonance is wasted. Moreover, wide-band, high-power RF amplifiers are not energy-efficient, often requiring a heat-sink and fan to dissipate heat. As a result, these sensor readers are expensive and bulky. Furthermore, in the case of a sensor with multiple LC circuits, resonant frequencies from each of the LC circuits must be read. A single PLL circuit, however, cannot read multiple frequencies simultaneously. Thus, multiple PLL circuits are required with those sensor readers to simultaneously read multiple frequencies. This results in complex readers that are both large and expensive.

In some simplified reader systems, which seek to simplify reader circuitry and control software/hardware as well as address power consumption, the reader may be designed to fire an RF pulse only at a fixed center frequency (with a limited frequency bandwidth) at or near the center of the sensor's operating frequency range. However, the limited frequency bandwidth of the fixed frequency must cover the sensor's operating frequency range; otherwise, some of the sensor's frequency responses may be out of the reader's measurement range. The wider the sensor's operating frequency range, the wider the reader's frequency bandwidth must be. At the end, a relatively wide-band RF amplifier may be required, which is not energy efficient, as discussed above. If a reader is configured with a limited frequency bandwidth at a fixed center frequency, the reader doesn't have a uniform SNR over the sensor's operating frequency range; the highest SNR occurs only when the sensor's resonant frequency is at the reader's fixed center frequency, and the SNR decreases as the sensor's resonant frequency moves away from the reader's fixed center frequency. Moreover, for a pressure sensor with a wide pressure response range, if a reader is configured with a narrow frequency bandwidth at a fixed center frequency, the sensitivity of the sensor (i.e., the frequency change vs. the pressure change) may have to be decreased for the reader to cover its frequency range. As a result, measurement error may increase with decreased sensitivity. Further, a reader only firing at a fixed center frequency may not be able to simultaneously read multiple different resonant frequencies of a sensor with multiple LC circuits, in which different resonant frequencies must be separated.

Accordingly, a need exists for an efficient, wide-band, and compact sensor reader that improves energy efficiency by operating without a high power RF amplifier and/or reads a wide range of resonant frequencies and multiple resonant frequencies simultaneously, without requiring a wide-band signal generator. These readers could be more compact, energy efficient, and cost-effective.

As discussed below, several embodiments of the present disclosure address some or all of these issues as well as providing additional advantages.

SUMMARY

According to some embodiments, a wireless sensor reader interrogates a wireless LC sensor to determine the resonant frequency of the LC circuit. In some embodiments, a wireless sensor reader interrogates multiple wireless LC sensors simultaneously to determine their resonant frequencies. These sensor readers are energy-efficient, compact, and can operate without requiring a high-power RF amplifier or a wide-band RF signal generator.

In one example, a wireless sensor reader for an implanted sensor includes a pulser configured to generate an excitation energy pulse; an antenna configured to transmit the excitation energy pulse to excite a wireless sensor, causing the wireless sensor to emit a ring-down signal, and to receive the ring-down signal from the sensor, the antenna having a ferrite backing shield; a receiver configured to receive the ring-down signal from the antenna and to amplify the ring-down signal; a data acquisition circuit configured to acquire the ring-down signal from the receiver and digitize the ring-down signal; and a processing unit including a processor, the processing unit configured to receive the digitized ring-down signal, digitally filter out noise from the ring-down signal, and to compute the resonant frequency of the ring-down signal.

In one variation of that example, the pulser uses a capacitor discharging technique to generate the excitation energy pulse.

In one variation of that example, the energy pulse is a spike-shape, low-energy, high-amplitude radio frequency pulse, with a pulse energy from about 10 uJ to about 100 uJ, an amplitude from about 100 volts to about 1000 volts, and a pulse width from about 5 ns to about 50 ns.

In one variation of that example, the antenna of the reader is a single loop antenna.

In one variation of that example, the antenna of the reader is inductively coupled with a sensor's antenna.

In one variation of that example, the processing unit first applies a digital Fourier Transform to the ring-down signal and then uses the Fourier Transform of the ring-down signal to identify the resonant frequency.

In one variation of that example, the sensor further comprises a timing and trigger circuit and a logic control circuit configured to: place the pulser, the receiver, and the data acquisition circuit into an idle mode when not in use; and power up the pulser, the receiver, and the data acquisition circuit at a predetermined time interval.

In one variation of that example, the sensor further comprises a high-pass filter and a low-pass filter to filter out unwanted frequency information from the ring-down signal.

DETAILED DESCRIPTION

Figure 1:
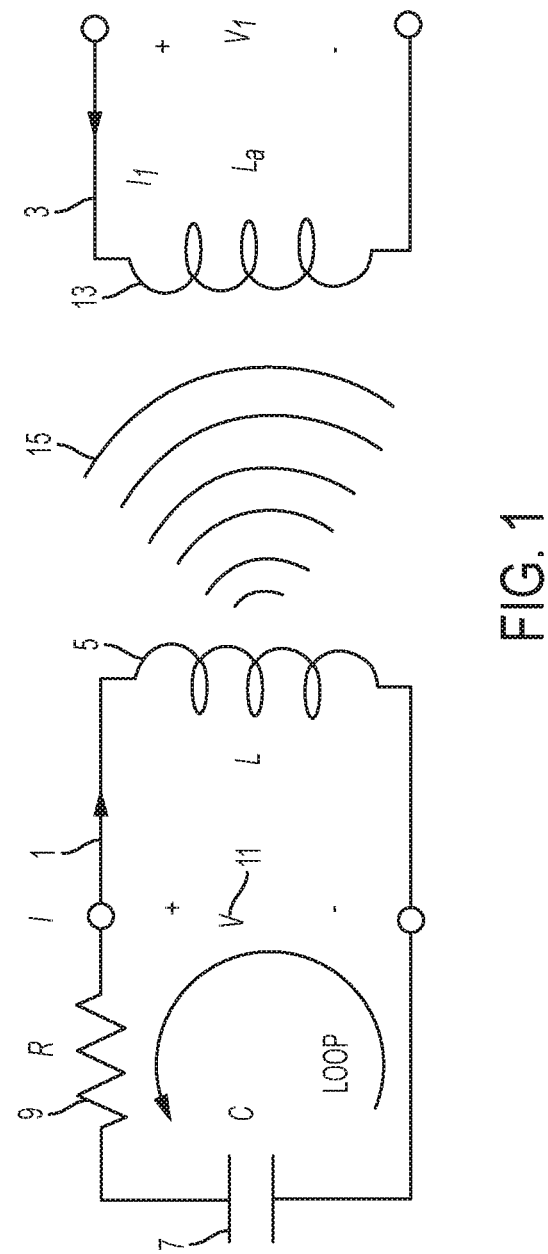
FIG. 1 illustrates a diagram of an exemplary LC tank circuit and a portion of an exemplary monitoring circuit, according to embodiments of the present disclosure.

According to some embodiments, FIG. 1 shows an electrical equivalent resonant circuit 1 of a passive LC sensor with an equivalent capacitor C (reference number 7) and inductor L (reference number 5), and an electrical equivalent circuit 3 of a sensor reader, where the reader antenna 13 wirelessly measures the resonant frequency of the electrical equivalent resonant circuit 1 by magnetic induction between the sensor antenna (the inductor 5) and reader antenna 13. The electrical equivalent resonant circuit 1 can also be referred to as an LC circuit 1, LC tank, or LC tank circuit, because of the voltage 11 that it can store. The LC tank 1 has a resonant frequency that depends on the inductance and capacitance provided by the inductor 5 and capacitor 7, respectively. If the capacitor C (reference number 7) is configured to vary its capacitance in response to changes in pressure or other parameters within a vessel (such as temperature), the LC circuit 1 may work as a pressure sensor or a temperature sensor accordingly. As one of skill in the art will readily appreciate, there are a wide variety of electrical components that exhibit capacitive and inductive characteristics and that can be used in various embodiments discussed herein. As also shown in FIG. 1, the LC circuit 1 also includes an equivalent resistor 9 that represents energy loss due to RF absorption. In general, a smaller resistance loss is required to provide a higher quality factor (Q, e.g., greater than 35) so that the ring-down signal from the sensor 15 can last long enough for the reader to pick up the resonance signal.

One of the benefits of an LC tank (e.g., LC tank 1 in FIG. 1) is that characteristics of that circuit (e.g., resonant frequency) can be made without needing to include a power source, such as a battery, as part of the sensor circuit. Instead, an external reader or monitoring tool (e.g., circuit 3 in FIG. 1) can interact wirelessly with that circuit to detect those characteristics of the LC tank. These advantages render the LC tank as a suitable candidate for a pressure sensor for wirelessly monitoring blood pressure within a vessel.

For example, if a dielectric material that reacts to external pressure is placed within the capacitor (e.g., capacitor 7 in FIG. 1), a change in blood pressure will cause a change in capacitance in the LC tank, which results in a change in its resonant frequency. For another example, the LC tank 1 may be set up so that the plates of the capacitor 7 move in response to external pressures, which will affect the capacitance and the resonant frequency of the LC tank 1. Under either approach, if the other characteristics of the LC tank (e.g., inductance) remain relatively constant, the change in the resonant frequency can be used to determine the change in capacitance, which can then be used to determine a measurement of the blood pressure within the vessel.

Figure 2:
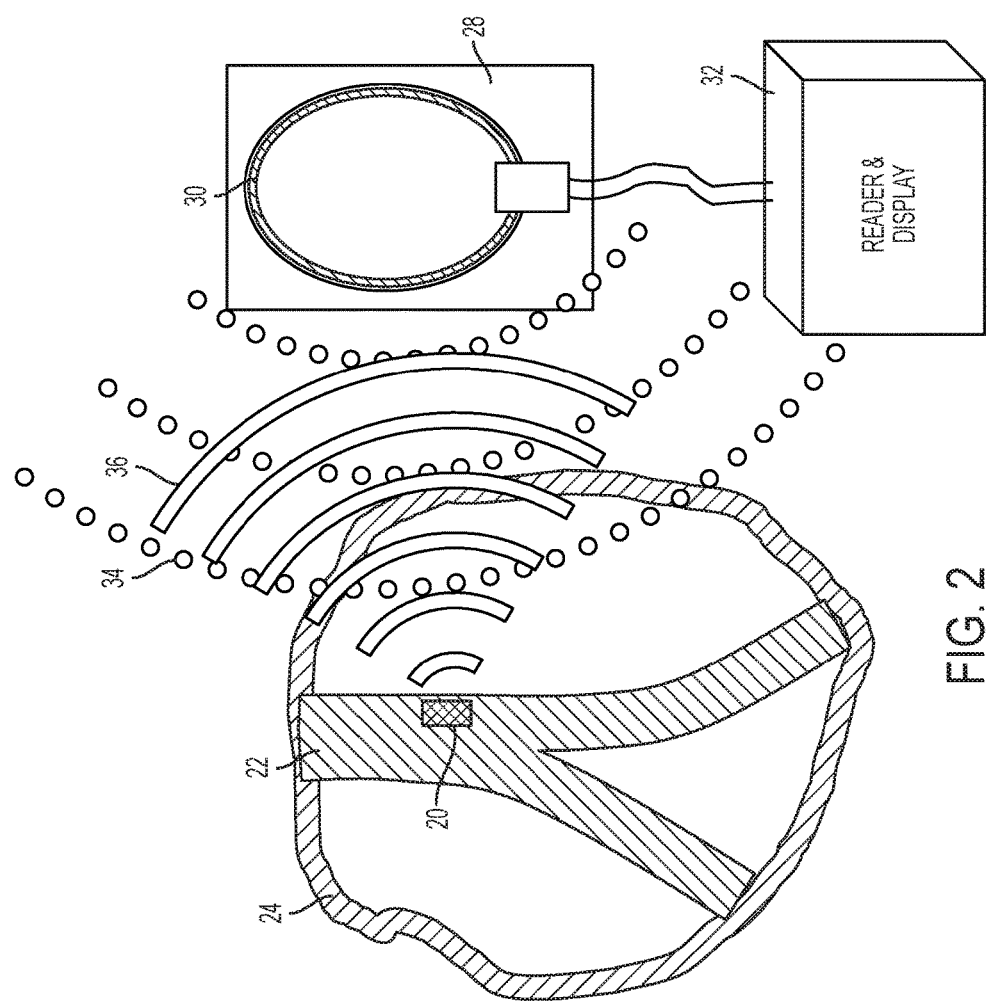
FIG. 2 illustrates an exemplary pressure sensor coupled to a stent-graft as well as an exemplary measuring tool, according to embodiments of the present disclosure.

These approaches can be seen in FIG. 2, in which a pressure sensor 20 uses an LC circuit to monitor blood pressure at a stent-graft 22 placed to treat an aneurism in the body 24. In various embodiments, the pressure sensor may be placed on an outer surface of the stent-graft, an inner surface of the stent-graft, or may be integrated within the stent-graft. Thus, measuring blood pressure at the stent-graft includes measuring blood pressure outside of the stent-graft and/or within the stent-graft. The measuring device 28 includes an antenna 30 and a reader/display 32. The reader/display 32 can include a processing unit that has a processor, memory, and other hardware and/or software needed to measure signals from the antenna 30 and process those signals to determine (and perhaps display) the blood pressure measurements. The measuring device 28 emits a pulse 34, which causes the pressure sensor to emit a ring-down signal 36. The measuring device 28 analyzes the ring-down signal 36 to identify pressure within the stent-graft 22.

Figure 3B:
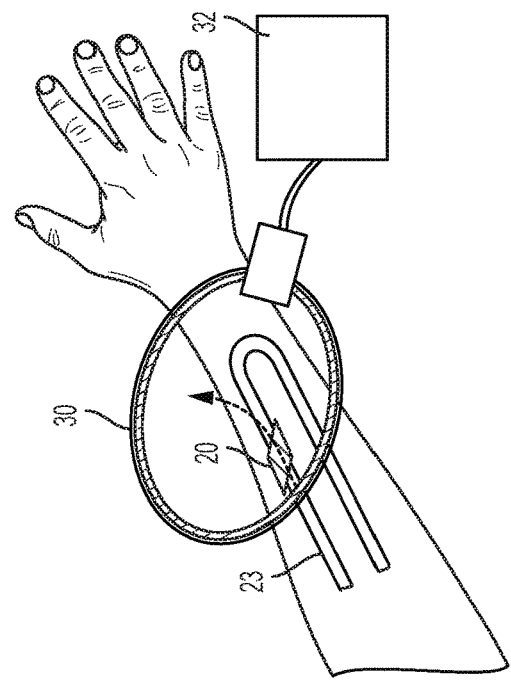
FIGS. 3A-3B illustrate an exemplary measurement technique, according to embodiments of the present invention.
Figure 3A:
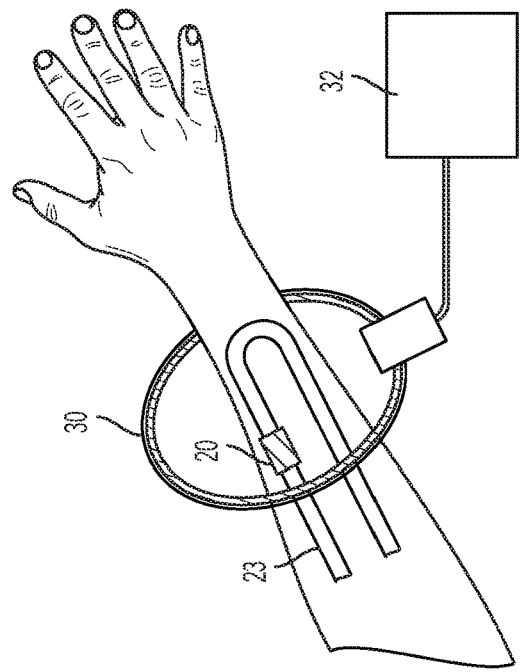

FIGS. 3A and 3B illustrate how the measurement device can extract a pressure measurement from a sensor 20. The antenna 30 of the measurement tool passes over the sensor 20, which is secured to a graft 23 within the patient. The antenna 30 transmits energy to the sensor 20, which responds by emitting RF energy at its resonant frequency. The antenna 30 detects this energy, determines the resonant frequency, and then computes the pressure within the graft 23. Alternatively, the antenna 30 may transmit energy along a spectrum of frequencies at different times, and monitor for when the sensor 20 begins to absorb energy, which will correspond to its resonant frequency.

An efficient reader seeks to deliver maximum energy into the LC circuit. One method is to fire a sinusoidal burst at the resonance frequency of the LC circuit, which may not be practical during the actual measurement since the resonant frequency to be measured is unknown. The other method is to send a very-short energy pulse into the LC circuit, which energizes the LC circuit instantly to its maximum energy level.

In some embodiments, an energy-efficient, wide-band and compact wireless sensor reader remotely interrogates an implanted wireless inductive-capacitive (LC) sensor. The wireless sensor reader uses a capacitor discharging technique to transmit an instantaneous, spike-shaped, high-amplitude, low-energy pulse to cause the wireless LC sensor to generate a ring-down signal. Instead of using an RF signal generator and power amplifier, the reader first stores electrical energy into one or more capacitors through electrical charging (i.e., energizing the capacitors), and then rapidly connects the charged capacitor(s) to the reader antenna 13 to release the energy (i.e., generating the energy pulse and transmitting that energy pulse to the LC circuit). As a result, the sensor's LC circuit is quickly energized through the magnetic coupling between the reader antenna 13 and sensor antenna (the inductor 5). The capacitor charging and discharging circuit is much simpler and less expensive compared to typical RF signal generators and power amplifiers. The energy of the pulse may range from about 10 uJ to about 100 uJ, with amplitudes from about 100 volts to about 1000 volts and pulse widths from about 5 ns to about 50 ns. In general, the excitation pulse width should be much smaller than the period of the resonance frequency; typically, the pulse width is about ⅕ or ¹⁄₁₀ of that period. For example, for a resonance signal with a period of 50 ns period (i.e., 20 MHz), the excitation pulse width can be 10 ns or less.

After exciting the sensor, the wireless sensor reader receives, amplifies, and filters the ring-down signal that is emitted from the excited sensor. The wireless sensor then digitizes the amplified ring-down signal using an analog-to-digital (ND) converter and sends the digitized signal to a processing unit. The processing unit uses hardware and/or software stored in a tangible, non-transitory medium and executed by a processor to analyze the digitized signal (e.g., by Fast Fourier Transformation) and determine the resonant frequency of the LC sensor. In some embodiments, the hardware (e.g., processor) of the sensor reader executes a threshold-peak detection technique. In this technique, the sensor reader takes the first derivative curve of the FFT signal of the measured ring-down signal and then smooths the derivative curve. Next, the sensor reader searches for peaks by looking for downward-going zero-crossings from the smoothed derivative curve. Finally, the sensor reader evaluates all the peak candidates and takes only the points where their peak amplitudes exceed a certain minimum (called the "peak amplitude threshold") and their peak widths exceed a certain predetermined minimum (called the "peak width threshold"). By carefully adjusting the smooth width, peak amplitude threshold, and peak width threshold, the processing unit of the sensor reader detects only the desired peaks and ignores peaks that are too small, too wide, or too narrow. The processing unit of the sensor reader may also use a digital filter to remove noise from the raw ring-down signal.

Figure 4:
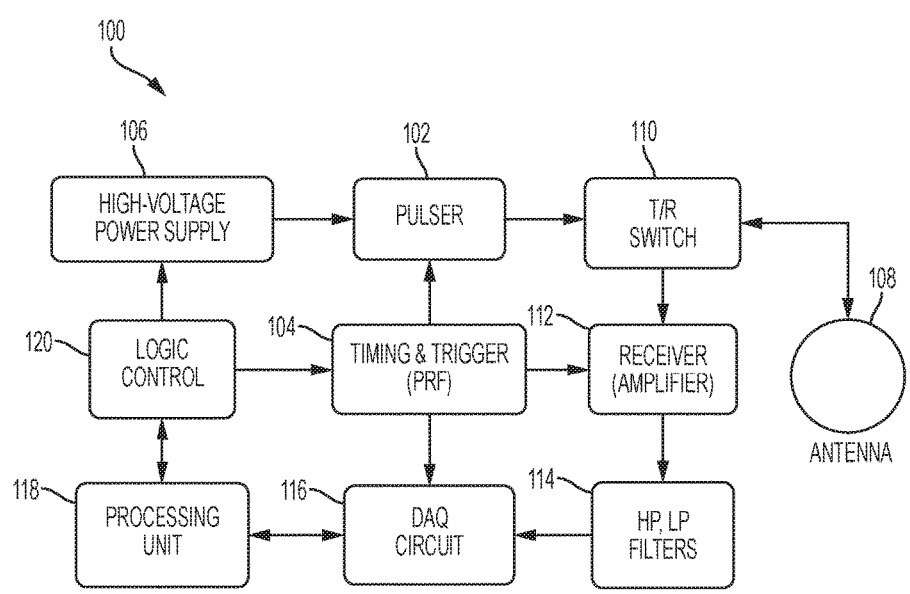
FIG. 4 illustrates components of an exemplary sensor reader, according to embodiments of the present disclosure.

In some embodiments, a sensor reader includes specific components designed to provide particular advantages, and some of those components are shown in FIG. 4. Specifically, a sensor reader 100 includes a pulser 102 (e.g., a pulser circuit or pulser module) that generates an electrical spike-shaped energy pulse, using a capacitor discharging technique, at predetermined intervals. The sensor reader 100 includes a timing and trigger circuit (timing/trigger circuit) or module 104 that controls the pulse repetition frequency (PRF), or the intervals at which the pulser circuit generates those pulses. A power supply or high-voltage DC supply 106 provides energy to charge the discharging capacitor(s) of the pulser 102.

The sensor reader 100 may include a transmission/receiving (T/R) switch 110. In the transmission mode, the activated pulser 102, discharging its capacitor's energy, causes an antenna 108 to transmit the excitation energy pulse to excite a sensor nearby (e.g., within a patient). During excitation of the sensor, the T/R switch 110 is set to a transmission mode and a receiver or amplifier 112 is cut off for protection from the high-voltage pulse impact.

The capacitor discharging technique used by the pulser 102 generates a RF energy pulse in a very short time, for example, from a few to about one hundred nanoseconds, and with an amplitude of several hundred volts. This pulse can excite an implanted LC sensor deep in a human body (for example, 10 to 25 cm deep within the patient) if the reader antenna 13 and the sensor antenna (the inductor 5) are properly coupled. Since the excitation pulse width is very short, this energy pulse can simultaneously excite multiple LC circuits at a wide range of frequencies. As discussed before, the cutoff frequency of the pulse excitation may approximate ⅕ of the reciprocal of the excitation pulse width. For example, a 5 ns pulse can excite LC circuits at 10 MHz, 15 MHz, 25 MHz or 40 MHz (as discussed in the examples below). In some embodiments, the antenna 108 has a ferrite backing shield, or a similar material, to eliminate potential interference from a nearby conductor.

After receiving the energy pulse, the sensor emits a ring-down signal. The antenna 108 acquires the ring-down signal, which is then transmitted to rest of the sensor reader 100 once the T/R switch 110 changes to a receiving mode. In some embodiments, the sensor reader 100 is set to automatically switch the T/R switch 110 into the receiving mode shortly after (for example, less than 10 ns delay) or immediately after the energy pulse is transmitted. The receiver 112 receives the ring-down signal from the antenna 108 and then amplifies the signal. The amplified signal then passes through high-pass and low-pass filters 114. A data acquisition circuit or module 116 (a DAQ circuit or a DAQ module) digitizes the ring-down signal, using an analog-to-digital (A/D) converter, and transfers the digitized ring-down signal to the processing unit 118. The processing unit 118 computes a Fast Fourier Transform (FFT) of the digitized ring-down signal and then locates the resonant frequency of the LC sensor by a threshold-peak detection technique. In some embodiments, the processing unit 118 executes software to compute the FFT and locate the resonant frequency. The sensor reader 100 may also include logic control 120 that governs the actions of the high-voltage DC supply 106 and the timing and trigger circuit 104.

In some embodiments, the timing and trigger circuit, a logic control circuit, and/or a processing unit places the pulser, the receiver, and the data acquisition circuit (and/or other components) into an idle mode when not in use, and powers up the pulser, the receiver, and the data acquisition circuit (and/or other components) at a predetermined time interval. As one of skill will readily appreciate, there are a variety of hardware and/or software components that can be configured to perform the individual functions of the components highlighted in FIG. 4, including specific hardware and/or software that can perform the functions of multiple components.

Figure 5:
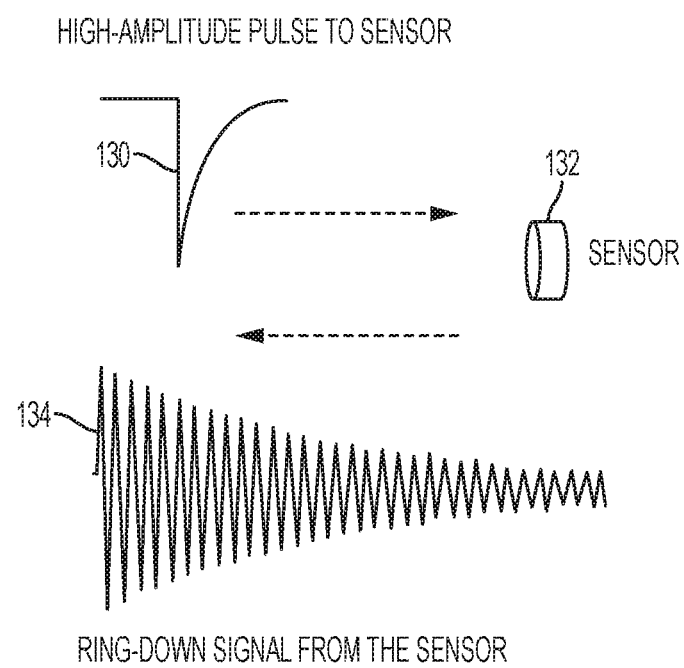
FIG. 5 illustrates a high-amplitude pulse transmitted to a sensor as well as a ring-down signal transmitted by the sensor, according to embodiments of the present disclosure.
Figure 6:
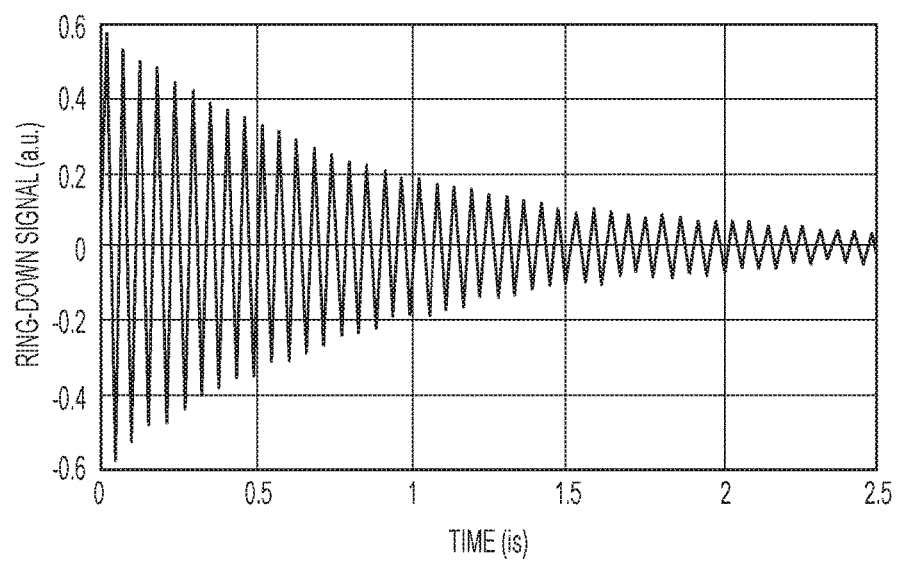
FIG. 6 illustrates an exemplary ring-down signal, according to embodiments of the present disclosure.
Figure 7:
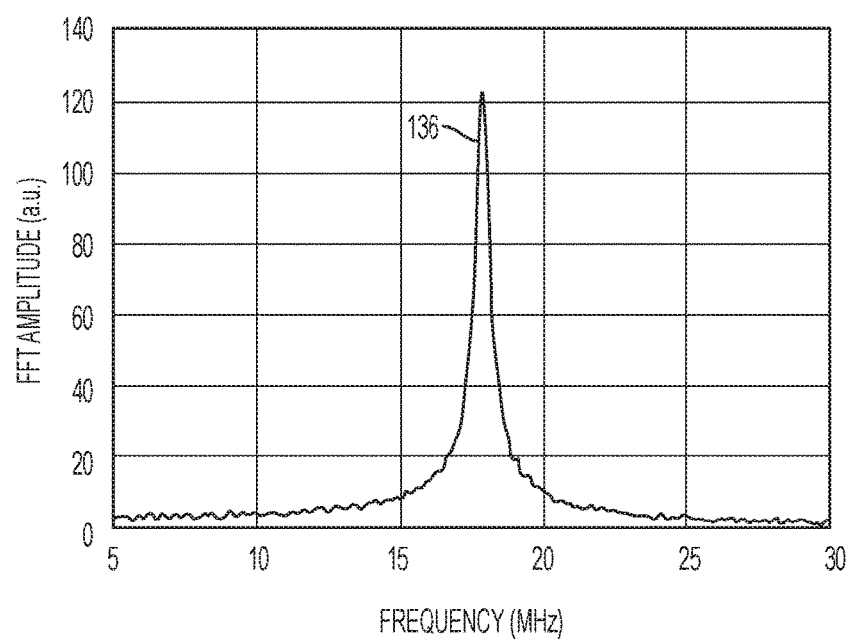
FIG. 7 illustrates FFT amplitudes of the ring-down signal of FIG. 6.
Figure 8:
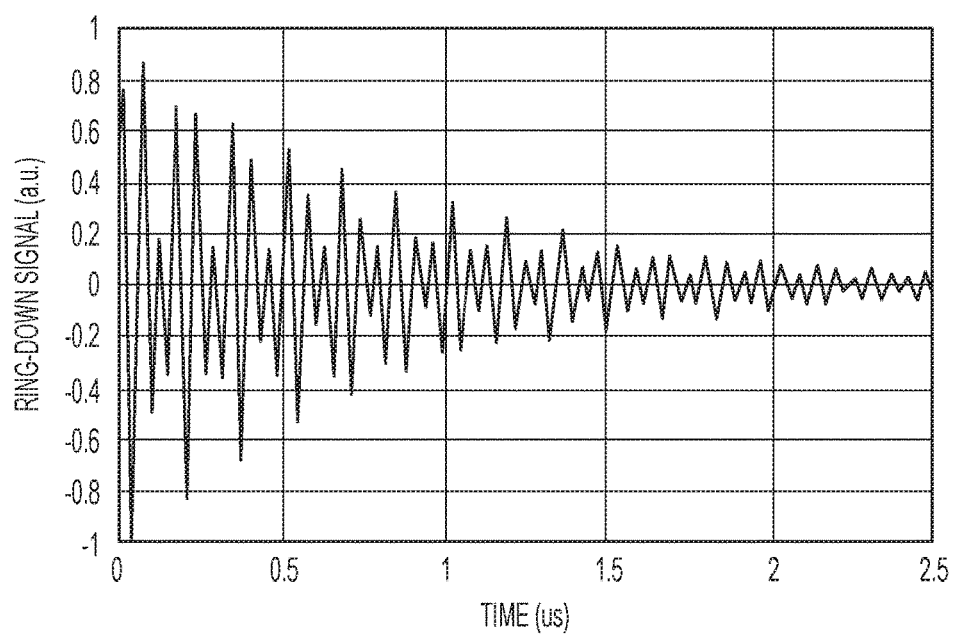
FIG. 8 illustrates an exemplary ring-down signal from a sensor having multiple LC circuits, according to embodiments of the present disclosure.
Figure 9:
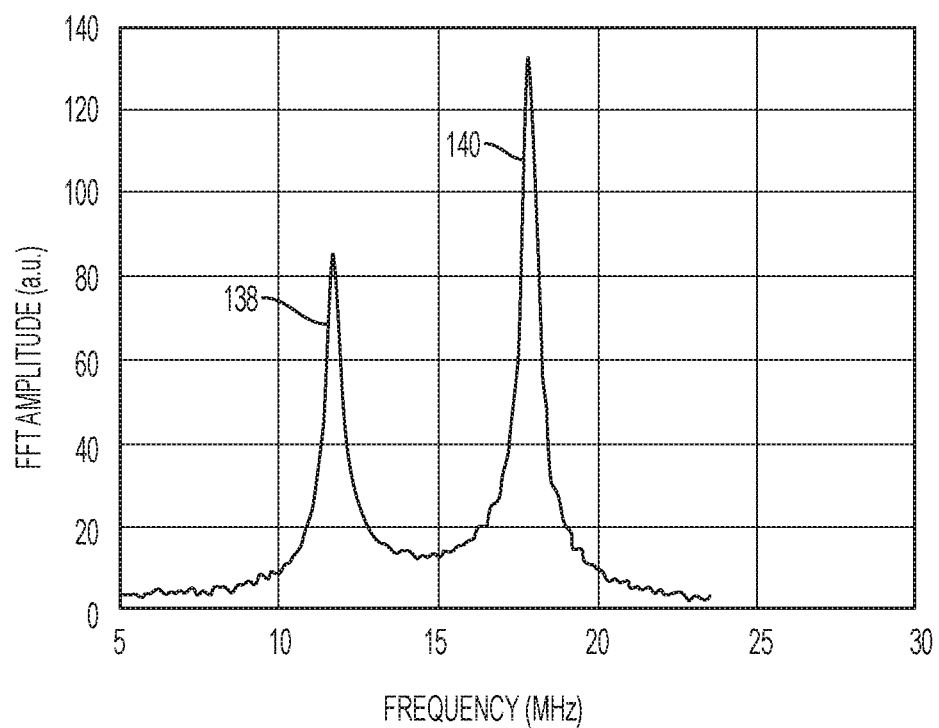
FIG. 9 illustrates FFT amplitudes of the ring-down signal of FIG. 8.

An example of an energy pulse 130 transmitted to an LC sensor 132, as well as a ring-down signal 134 received from the sensor, is shown in FIG. 5. Another example of a ring-down signal is shown in FIG. 6. The FFT for that signal is shown in FIG. 7, in which a peak 136 corresponds to the resonant frequency. In the case of a sensor with multiple LC circuits, multiple resonant frequencies from different LC circuits can be determined simultaneously. For example, FIG. 8 shows an exemplary ring-down signal for such a sensor. The FFT for that signal is shown in FIG. 9, in which peaks 138 and 140 correspond to the different resonant frequencies for the different LC circuits.

Figure 10:
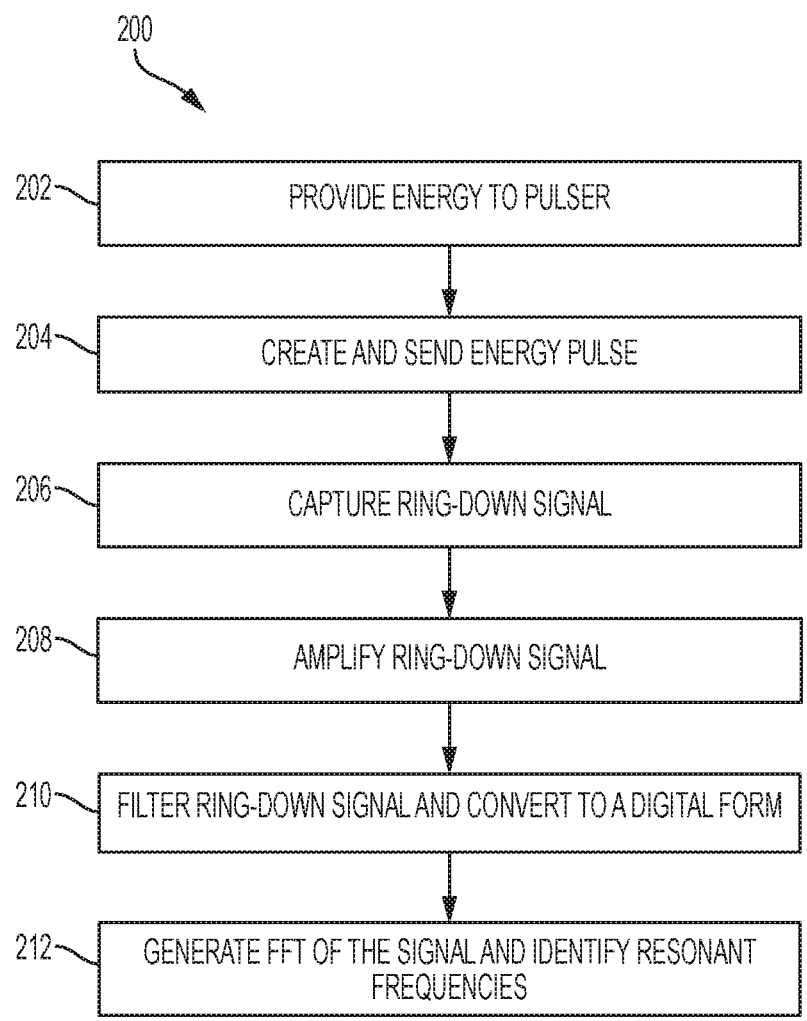
FIG. 10 illustrates steps taken by an exemplary sensor reader to identify resonant frequencies of a sensor, according to embodiments of the present disclosure.

An exemplary process 200 for determining the resonant frequency of an LC pressure sensor is shown in FIG. 10. In step 202, a power supply (e.g., 106 in FIG. 4) provides energy to a pulser (e.g., 102 in FIG. 4). For example, the energy from the energy supply is used to charge capacitors within the pulser. Next, a T/R switch (e.g., 110 in FIG. 4) is set to a transmission mode and the pulser creates an electrical, spike-shape energy pulse, using a capacitor discharging technique, and sends that energy pulse to the antenna (e.g., 108 in FIG. 4), step 204. In some embodiments, creating and sending that energy pulse is governed by a timing and trigger circuit (e.g., 104 in FIG. 4), and can be repeated at set intervals defined by the timing and trigger circuit.

The energy pulse is received by an LC sensor. In response, the LC sensor emits a ring-down signal. In step 206, the antenna 108 captures the ring-down signal. The T/R switch changes to a receiving mode to transmit the ring-down signal from the antenna 108 to a receiver (e.g., 112 in FIG. 4), which amplifies the ring-down signal, step 208. In some embodiments, the operations of the T/R switch are automatically controlled by the timing and trigger circuit, by a processing unit (e.g., 118 in FIG. 4), and/or by other logic (e.g., 120 in FIG. 4). The exact timing of when the T/R switch changes modes may vary, so long as the T/R switch is set to the transmission mode when the pulser sends the pulse and to the receiving mode when receiving the signal from the antenna 108.

In step 210, the amplified ring-down signal is filtered and converted to a digital signal (e.g., using low-pass filters 114 and DAQ circuit 116). The processing unit then receives the ring-down signal. In step 212, the processing unit generates an FFT for that signal and identifies the frequency peak (or peaks), which correspond to the resonant frequency (or frequencies) of the LC circuit (or circuits) within the pressure sensor.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A wireless sensor reader for an implanted sensor, comprising:
   a pulser configured to generate an excitation energy pulse, wherein the pulser uses a capacitor discharging technique to generate the excitation energy pulse;
   an antenna configured to transmit the excitation energy pulse to excite a wireless sensor, causing the wireless sensor to emit a ring-down signal, and to receive the ring-down signal from the wireless sensor, the antenna having a ferrite backing shield;
   a receiver configured to receive the ring-down signal from the antenna and to amplify the ring-down signal;
   a data acquisition circuit configured to acquire the ring-down signal from the receiver and digitize the ring-down signal; and
   a processing unit including a processor, the processing unit being configured to receive the digitized ring-down signal, digitally filter out noise from the ring-down signal, and to compute a resonant frequency of the wireless sensor.

2. The wireless sensor reader of claim 1, wherein the excitation energy pulse is a spike-shaped, low-energy, high-amplitude radio frequency pulse, with a pulse energy from about 10 uJ to about 100 uJ, an amplitude from about 100 volts to about 1000 volts, and a pulse width from about 5 ns to about 50 ns.

3. The wireless sensor reader of claim 1, wherein the antenna of the wireless sensor reader is a single loop antenna.

4. The wireless sensor reader of claim 1, wherein the antenna of the wireless sensor reader is inductively coupled with a sensor's antenna.

5. The wireless sensor reader of claim 1, wherein the processing unit first applies a digital Fourier Transform to the ring-down signal and then uses the Fourier Transform of the ring-down signal to identify the resonant frequency.

6. The wireless sensor reader of claim 1, further comprising a timing/trigger circuit and a logic control circuit, configured to:
   place the pulser, the receiver, and the data acquisition circuit into an idle mode when not in use; and
   power up the pulser, the receiver, and the data acquisition circuit at a predetermined time interval.

7. The sensor reader of claim 1, further comprising a high-pass filter and a low-pass filter to filter out unwanted frequency information from the ring-down signal.

8. A method for operating a sensor reader to identify one or more resonant frequencies of an LC sensor implanted within a human body, the method comprising:
   energizing one or more capacitors under the control of a pulser;
   setting a T/R switch to a transmission mode;
   generating a spike-shaped, low-energy, high-amplitude radio frequency pulse using the one or more capacitors;
   transmitting the spike-shape, low-energy, high-amplitude radio frequency pulse to an LC sensor through an antenna;
   receiving, using the antenna, a ring-down signal sent from the LC sensor in response to the spike-shaped, low-energy, high-amplitude radio frequency pulse;
   setting the T/R switch to a receiving mode; and
   processing the ring-down signal to identify one or more resonant frequencies of the LC sensor.

9. The method of claim 8, wherein processing the ring-down signal to identify the one or more resonant frequencies of the LC sensor includes filtering the ring-down signal.

10. The method of claim 8, wherein processing the ring-down signal to identify the one or more resonant frequencies of the LC sensor includes generating a Fast Fourier Transform of the ring-down signal.

11. The method of claim 10, wherein processing the ring-down signal to identify the one or more resonant frequencies of the LC sensor further includes identifying peak candidates using downward-going zero-crossings from a derivative curve of the Fast Fourier Transform of the ring-down signal.

12. The method of claim 11, wherein processing the ring-down signal to identify one or more resonant frequencies of the LC sensor further includes selecting peak candidates whose peak amplitudes exceed a peak amplitude threshold, and whose peak widths exceed a peak width threshold.

13. A wireless sensor reader for an implanted sensor, comprising:
   an antenna configured to transmit an excitation energy pulse to excite a wireless sensor and to receive a ring-down signal sent from the sensor in response to the excitation energy pulse;
   a pulser configured to generate the excitation energy pulse using a capacitor discharging technique;
   a receiver configured to receive the ring-down signal from the antenna and to amplify the ring-down signal;
   a T/R switch configured to automatically transition between a transmission mode, in which the pulser is electrically connected to the antenna and the receiver is shielded from the pulser, and a receiving mode, in which the receiver is electrically connected to the antenna and the pulser is shielded from the receiver; and
   a processing unit including a processor, the processing unit being configured to receive the ring-down signal, digitally filter out noise from the ring-down signal, and to compute a resonant frequency of the wireless sensor.

14. The wireless sensor reader of claim 13, wherein the wireless sensor comprises multiple LC circuits and wherein the processing unit is configured to identify a resonant frequency for each LC circuit of the multiple LC circuits.

15. The wireless sensor reader of claim 13, wherein the pulser is configured to generate the excitation energy pulse at predetermined intervals.

16. The wireless sensor reader of claim 15, wherein the T/R switch is configured to automatically transition between the transmission mode and the receiving mode at predetermined intervals.

17. The wireless sensor reader of claim 16, further comprising a timing and trigger module configured to govern the predetermined intervals at which the pulser is configured to generate the excitation energy pulse and at which the T/R switch is configured to automatically transition between the transmission mode and the receiving mode.

18. The wireless sensor reader of claim 13, wherein the excitation energy pulse generated by the pulser can excite LC circuits at 10 MHz, 15 MHz, 25 MHz, or 40 MHz.

19. The wireless sensor reader of claim 13, wherein the pulser generates the excitation energy pulse in less than 100 nanoseconds.

* * * * *